(12) United States Patent
Brownlee

(10) Patent No.: US 8,568,380 B2
(45) Date of Patent: Oct. 29, 2013

(54) DIAPERING SYSTEM USING RE-USABLE DIAPER SHELL WITH REPLACEABLE ABSORBENT INSERT AND METHOD OF MANUFACTURE OF SAME

(76) Inventor: James Roy Brownlee, Vancouver (CA)

(\*) Notice: Subject to any disclaimer, the term of this patent is extended or adjusted under 35 U.S.C. 154(b) by 729 days.

(21) Appl. No.: 12/375,172

(22) PCT Filed: Aug. 2, 2007

(86) PCT No.: PCT/CA2007/001370
§ 371 (c)(1),
(2), (4) Date: Feb. 20, 2009

(87) PCT Pub. No.: WO2008/014621
PCT Pub. Date: Feb. 7, 2008

(65) Prior Publication Data
US 2010/0241098 A1    Sep. 23, 2010

Related U.S. Application Data

(60) Provisional application No. 60/821,246, filed on Aug. 2, 2006.

(51) Int. Cl.
*A61F 13/15* (2006.01)

(52) U.S. Cl.
USPC ............ 604/385.14; 604/385.15; 604/385.28; 604/385.31

(58) Field of Classification Search
USPC .......... 604/385.14, 385.15, 385.28, 394–398, 604/385.31, 385.04
See application file for complete search history.

(56) References Cited

U.S. PATENT DOCUMENTS

| | | |
|---|---|---|
| 3,865,110 A | 2/1975 | Traverse |
| 3,927,674 A | 12/1975 | Schaar |
| 4,034,760 A | 7/1977 | Amirsakis |
| 4,085,753 A | 4/1978 | Gellert |
| 4,493,713 A | 1/1985 | Izzo |
| 4,496,359 A | 1/1985 | Pigneul |

(Continued)

FOREIGN PATENT DOCUMENTS

| | | |
|---|---|---|
| CA | 2027234 | 5/1991 |
| EP | 0430443 A1 | 6/1991 |

(Continued)

OTHER PUBLICATIONS

International Search Report issued in respect of Patent Cooperation Treaty Application No. PCT/CA1997/000634 on May 25, 1998.

(Continued)

*Primary Examiner* — Lynne Anderson
(74) *Attorney, Agent, or Firm* — Bruce M. Green; Oyen Wiggs Green & Mutala LLP

(57) ABSTRACT

A two-piece diaper system having a re-usable shell and a removable and replaceable absorbent pad is provided. The re-usable diapering system consists of a non-absorbent outer liquid impervious shell, as in a standard disposable diaper but without an integral central absorbent layer which is exposed to liquids in the crotch area. A separate disposable absorbent pad is provided in the central crotch area of the disposable diaper which is not sandwiched in the shell. The central area of the shell is stiffened to facilitate manufacture and handling by the user.

22 Claims, 8 Drawing Sheets

(56) References Cited

U.S. PATENT DOCUMENTS

| | | | |
|---|---|---|---|
| 4,578,073 | A | 3/1986 | Dysart et al. |
| 4,579,556 | A | 4/1986 | McFarland |
| 4,597,761 | A | 7/1986 | Buell |
| 4,604,096 | A | 8/1986 | Dean et al. |
| 4,743,240 | A | 5/1988 | Powell |
| 4,834,737 | A | 5/1989 | Khan |
| 4,923,455 | A | 5/1990 | Dean et al. |
| 4,931,052 | A | 6/1990 | Feldman |
| 4,964,857 | A | 10/1990 | Osborn |
| 4,968,312 | A | 11/1990 | Khan |
| 5,071,414 | A | 12/1991 | Elliott |
| 5,141,505 | A | 8/1992 | Barrett |
| 5,217,447 | A | 6/1993 | Gagnon |
| 5,304,158 | A | 4/1994 | Webb |
| 5,360,422 | A | 11/1994 | Brownlee et al. |
| 5,405,342 | A | 4/1995 | Roessler et al. |
| 5,409,476 | A | 4/1995 | Coates |
| 5,458,591 | A | 10/1995 | Roessler et al. |
| 5,476,457 | A | 12/1995 | Roessler et al. |
| 5,613,959 | A | 3/1997 | Roessler et al. |
| 5,778,110 | A | 7/1998 | Furuya |
| 6,015,935 | A | 1/2000 | LaVon et al. |
| 6,193,702 | B1 | 2/2001 | Spencer |
| 6,229,061 | B1 | 5/2001 | Dragoo et al. |
| 6,254,583 | B1 | 7/2001 | Coates |
| 6,450,996 | B1 | 9/2002 | Otsubo |
| 6,575,951 | B1 * | 6/2003 | Ono et al. ................. 604/385.14 |
| 6,579,273 | B2 | 6/2003 | Dupuy |
| 6,605,071 | B1 | 8/2003 | Gray et al. |
| 6,620,145 | B2 | 9/2003 | Nakaoka et al. |
| 6,623,466 | B1 | 9/2003 | Richardson |
| 6,689,113 | B2 * | 2/2004 | Boulanger et al. ........ 604/385.04 |
| 6,723,080 | B1 | 4/2004 | Habib et al. |
| 6,764,477 | B1 | 7/2004 | Chen et al. |
| 6,932,800 | B2 | 8/2005 | LaVon et al. |
| 6,989,005 | B1 | 1/2006 | LaVon et al. |
| 6,989,006 | B2 | 1/2006 | LaVon et al. |
| 7,166,095 | B1 * | 1/2007 | Coates ..................... 604/385.19 |
| 7,264,615 | B2 * | 9/2007 | Sherrod et al. ........... 604/385.14 |
| 7,431,716 | B2 | 10/2008 | Tracy |
| 7,491,196 | B2 | 2/2009 | Franke et al. |
| 2002/0029546 | A1 | 3/2002 | Gould |
| 2002/0065500 | A1 | 5/2002 | Rossi |
| 2003/0111168 | A1 | 6/2003 | Olson et al. |
| 2003/0199844 | A1 | 10/2003 | LaVon et al. |
| 2004/0078017 | A1 * | 4/2004 | Koyama et al. ................. 604/378 |
| 2004/0122401 | A1 * | 6/2004 | Van Gompel et al. ... 604/385.14 |
| 2005/0049569 | A1 | 3/2005 | Tracy |
| 2005/0215968 | A1 | 9/2005 | Henderson |
| 2010/0179497 | A1 * | 7/2010 | Brownlee ................. 604/385.14 |

FOREIGN PATENT DOCUMENTS

| | | |
|---|---|---|
| EP | 0684029 A2 | 11/1995 |
| EP | 0684029 A3 | 1/1997 |
| EP | 0763353 A2 | 3/1997 |
| GB | 1151321 | 5/1969 |
| GB | 2103930 | 3/1983 |
| GB | 2142541 | 1/1985 |
| GB | 2148095 | 5/1985 |
| GB | 2302026 | 1/1997 |
| GB | 2410439 | 8/2005 |
| WO | 85/03430 A1 | 8/1985 |
| WO | 93/23000 A1 | 11/1993 |
| WO | 94/03137 A1 | 2/1994 |
| WO | 94/15563 | 7/1994 |
| WO | 96/29037 A1 | 9/1996 |
| WO | 97/18785 | 5/1997 |
| WO | 99/12502 A1 | 3/1999 |
| WO | 2005072554 A1 | 8/2005 |
| WO | 2008/014621 A1 | 2/2008 |
| WO | 2008/095310 A1 | 8/2008 |

OTHER PUBLICATIONS

International Search Report issued in respect of Patent Cooperation Treaty Application No. PCT/CA2007/001370 on Nov. 26, 2007.
International Search Report issued in respect of Patent Cooperation Treaty Application No. PCT/CA2008/000257 on Jun. 2, 2008.
International Search Report issued in respect of Patent Cooperation Treaty Application No. PCT/CA2010/000050 on Apr. 29, 2010.

* cited by examiner

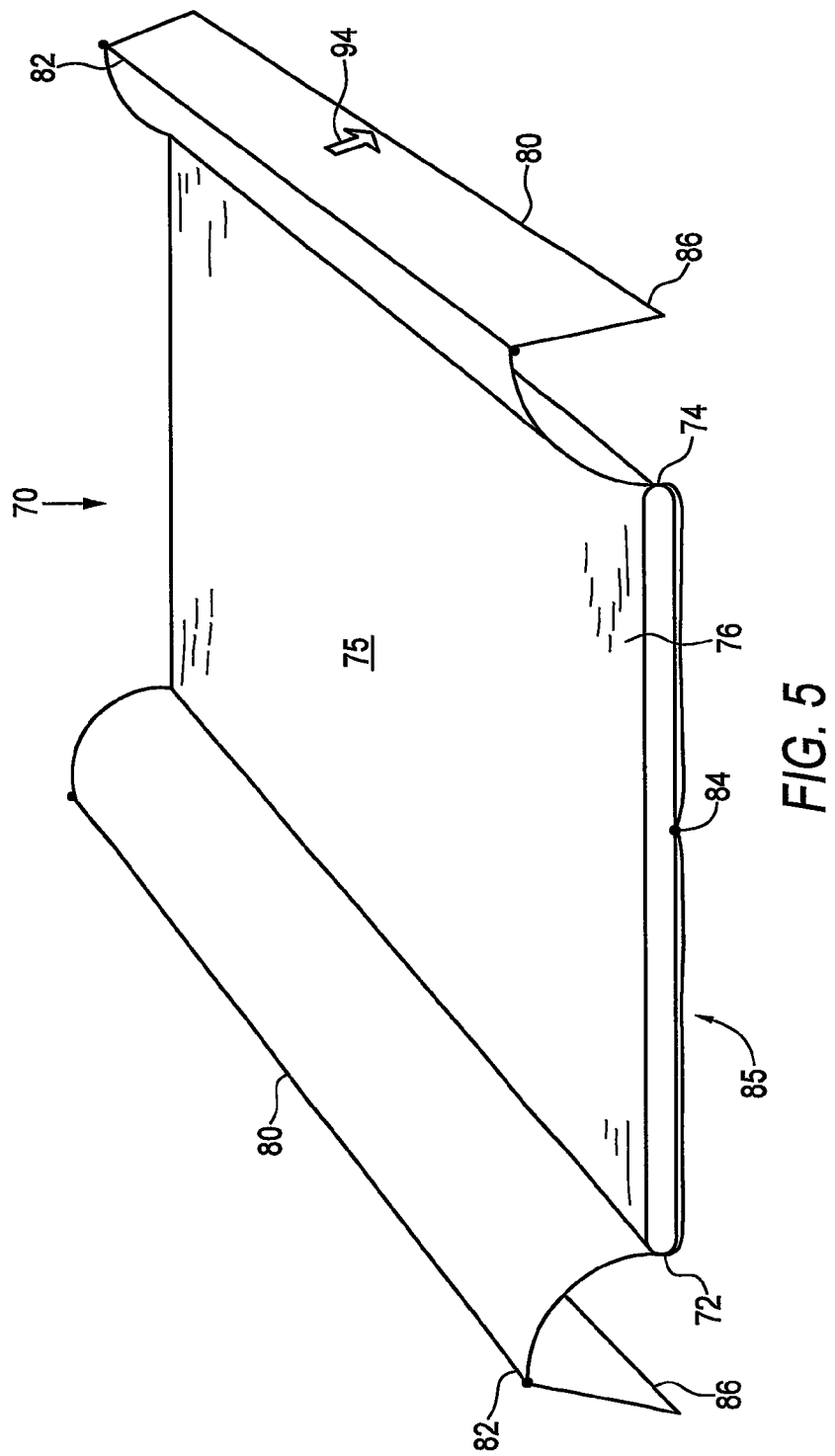

DIAPERING SYSTEM USING RE-USABLE DIAPER SHELL WITH REPLACEABLE ABSORBENT INSERT AND METHOD OF MANUFACTURE OF SAME

TECHNICAL FIELD

The invention relates to the construction of infant diapers, and particularly to a disposable diaper having a re-usable shell and a replaceable absorbent insert.

BACKGROUND

Currently most infant diapers are of the disposable variety. Machine washable cloth diapers are unpopular due to the expense, time and labor required to wash them and are more expensive in initial cost. Existing disposable diapers have a liquid impervious outer layer, an inner non-woven liner and an integral layer of absorbent material, typically pulp fluff, sandwiched between the inner and outer layers. Disposable diapers are not re-usable or recyclable. They create a large volume of waste, since the entire garment is disposed of after a single use. If the diaper is wetted or soiled even slightly, the entire diaper is discarded, at considerable expense and causing considerable waste.

There is a need for an infant diaper design which reduces the amount of waste, is re-usable and recyclable. There is a further need for an infant diaper design which assists in the goal of reducing a consumer's carbon footprint by reducing, re-using and recycling the plastic and hydrocarbon-based material. Various attempts have been made to solve this problem. The present inventor has disclosed, for example, in PCT international application, publication no. WO 99/12502, published 18 Mar. 1999, a diaper having a separate disposable absorbent pad in the central crotch area which was connected to the diaper by a releasable adhesive strip. Such design did not achieve acceptance due to the difficulty of manufacturing same and difficulty for the user in replacing and removing the absorbent insert, largely due to the instability of the pulp-free core of the shell as well as the difficulty in placement of the adhesive attachment. There is therefore a need for a diaper design which reduces waste, is re-usable and recyclable, readily manufactured and easy to use by the consumer and which reduces a consumer's carbon footprint by reducing, re-using and recycling the plastic and hydrocarbon-based material.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

Consequently, the present invention provides a two-piece diaper system having a re-usable shell and a removable and replaceable absorbent pad. The re-usable diapering system of the invention consists of a non-absorbent outer liquid impervious shell, as in a standard disposable diaper, and may have adhesive closures and elasticized legs, but without an integral central absorbent layer which is exposed to liquids in the crotch area. Rather, a separate disposable absorbent pad is provided in the central crotch area of the disposable diaper which is not sandwiched in the shell. The central area of the shell is stiffened to facilitate manufacture and handling by the user. The absorbent pad may have protective waterproof covers which extend over the leg gathers and may be removably secured by a releasable adhesive, in order to facilitate cleaning and reusing the shell.

The invention further provides a method of manufacturing the diaper in which the absorbent pad or material is not sandwiched into the diaper shell and the absorbent insert is separable from the shell and replacement inserts may be separately packaged. The present invention also provides a system with variable components to allow the consumer to select a particular level of performance and cost of the product.

The invention therefore provides a product and a method of manufacturing the product. The invention provides a diapering system comprising: a) a re-usable diaper shell comprising: i) a pliant non-absorbent, liquid impervious body for removable fitting to the wearer, forming an interior and an exterior surface, a front and back portion, opposed side edges and a crotch area when so fitted; ii) opposed, non-absorbent liner portions secured along the opposed side edges of the body and forming opposed elastically contractible leg cuffs extending between the front and back portion, the opposed elastically contractible leg cuffs thereby defining a central region between the opposed leg cuffs extending between the front and back portion, the central channel region being without absorbent material which is exposed to liquid in the crotch area and comprising in the central channel region a flexible material which is less pliant than said pliant body; and b) a removable, replaceable absorbent insert comprising an absorbent pad comprising a body of absorbent material having a non-woven hydrophilic covering, the insert being sized and shaped to be retained adjacent the interior surface of the diaper shell in the central region.

According to one aspect of the invention, the replaceable insert has attached hydrophobic covers extending from opposed sides of the pad, The protective covers may have elongated elastic members secured therein to form leg gathers when in operative position.

In addition to the exemplary aspects and embodiments described above, further aspects and embodiments will become apparent by reference to the drawings and by study of the following detailed descriptions.

BRIEF DESCRIPTION OF DRAWINGS

Exemplary embodiments are illustrated in referenced figures of the drawings. It is intended that the embodiments and figures disclosed herein are to be considered illustrative rather than restrictive.

In drawings which disclose a preferred embodiment of the invention:

FIG. 5 is a perspective view of the removable/replaceable absorbent pad of the invention;

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Figure 1:
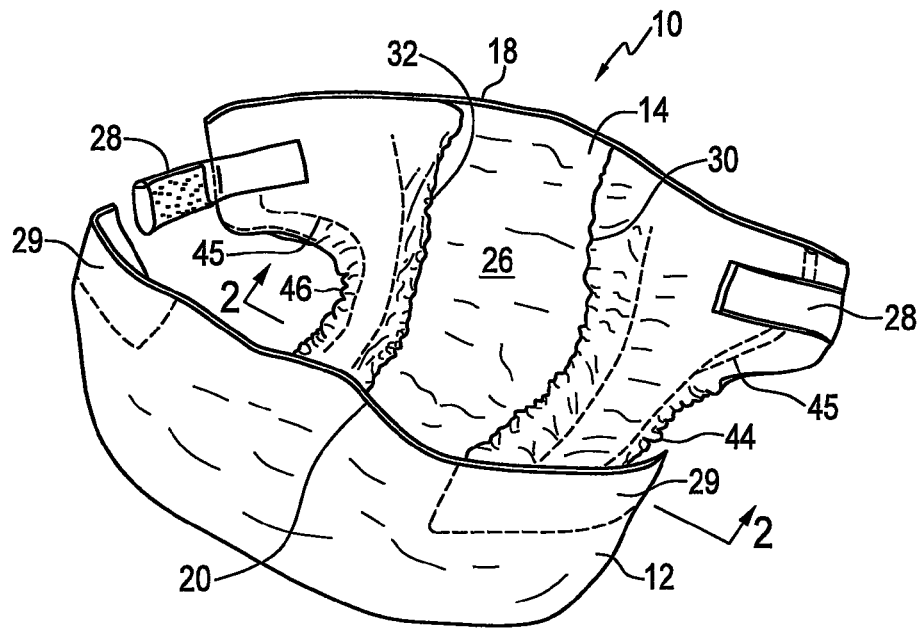
FIG. 1 is a perspective view of a conventional disposable infant diaper.
Figure 2:
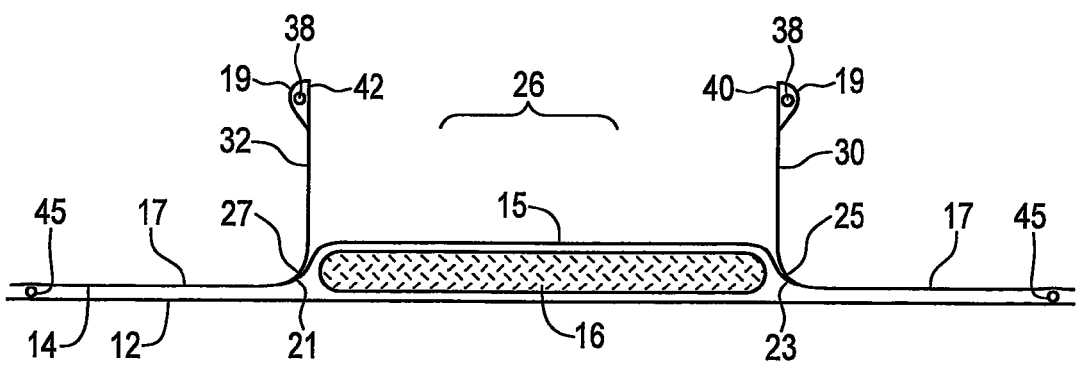
FIG. 2 is a cross-section taken along line 2-2 of FIG. 1 (not to scale)

FIGS. 1 and 2 illustrate a conventional disposable diaper 10. It is constructed of an hour-glass shaped backsheet 12 made of a lightweight liquid-impervious polyethylene plastic, a non-woven liner 14 made from a non-absorbent synthetic plastic such as non-woven polypropylene, and an absorbent pad 16 sandwiched between backsheet 12 and liner 14. The diaper has a back waist section 18, front waist section 20, and crotch area 26. Adhesive flaps 28 are provided to attach the garment around the infant. Areas 29 of high gloss polyethylene plastic film are provided on backsheet 12 to which adhesive strips 28 can releasably adhere without tearing the backsheet 12 on removal. Alternatively flaps 28 and sections 29 may comprise hook and loop fasteners. Elasticized interior leg gathers 30, 32 are formed in the non-woven liner with elastic members 38 running along inner edges 40, 42. Outside elastic leg cuffs are provided at 44, 46 with elastic members 45 provided at their outer edges. Elastic members 38, 45 are typically thin rubber ribbons, or a hot melt elastomeric adhesive may be used as is known in the disposable diaper art.

As illustrated in FIG. 2, the non-woven liner 14 of the conventional disposable diaper comprises three sections, an inner hydrophilic sheet 15 and outer hydrophobic sheets 17. Sheet 15 permits moisture to penetrate to pad 16 while keeping the skin of the infant away from the pad 16. Sheets 17 form the leg gathers 30, 32 which retain fecal matter and moisture in the central crotch area 26. Absorbent pad 16 is formed of pulp fluff material which is wrapped in a thin layer of absorbent paper tissue to maintain the integrity of the pad and prevent bunching of the fluff. Crystals of super absorbent polymers are typically distributed throughout the fluff to increase the absorbency of the pad 16.

In the existing manufacturing process, the two outer hydrophobic sheets 17 are first typically formed by slicing a tensioned sheet of the material and then forming outward folds 19 around elastic members 38. Sheet 15 is then glued or heat welded at either edge 21, 23 to outer sheets 17 along lines 25, 27. In a continuous process, non-woven liner 14, backsheet 12 and pad 16 are then glued or heat welded into a single unitary sandwich, with glue typically applied to the upper surface of backsheet 12 to secure pad 16 and liner 17. A few small spaced drops of glue are also applied to the top of pad 16 in spaced locations to attach it to sheet 15 and prevent movement of the pad 16.

Figure 3:
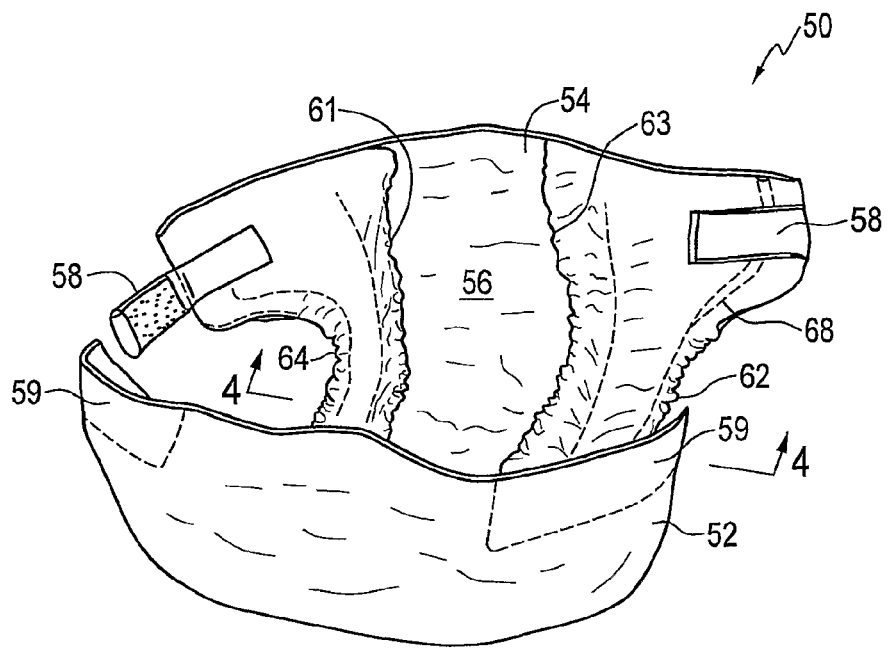
FIG. 3 is a perspective view of the re-usable non-absorbent infant diaper shell of the invention.
Figure 9:
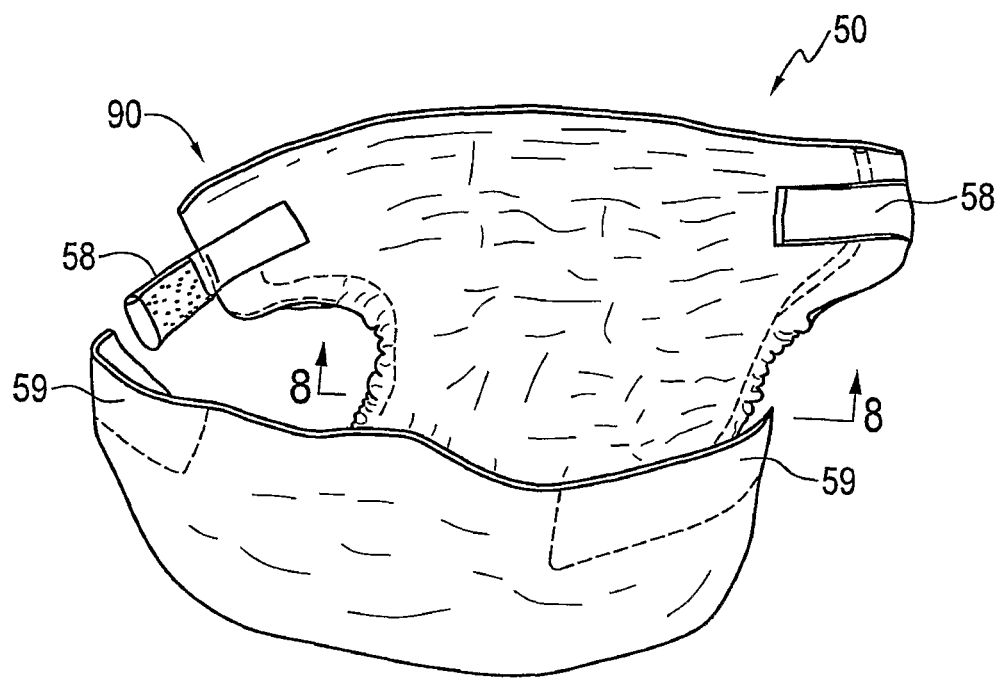
FIG. 9 is a is a perspective view of a second embodiment of the re-usable non-absorbent infant diaper shell of the invention.

The re-usable diaper shell 50 of the present invention is shown in FIGS. 3 and 4. The water-impermeable back sheet 52 and water impermeable liner sheet 54 are formed in a manner similar to the conventional disposable diaper 10, using conventional machinery for manufacturing disposable diapers, however no absorbent pad or material 16 is exposed to the interior in the crotch area 56. Instead, the inner layer 55 in crotch area 56 of liner sheet 54 may be a layer of waterproof plastic or non-woven, which is preferably stiffer and less pliant than the backer 52. Elasticized leg cuffs 62, 64 are formed by providing elastic members 68 between backer 52 and liner sheets 57. Interior leg gathers 61, 63 are formed with elastic members 65 within folds 69. The embodiment shown in FIG. 9 uses the same construction except no internal leg gathers 61, 63 are provided.

Figure 4A:
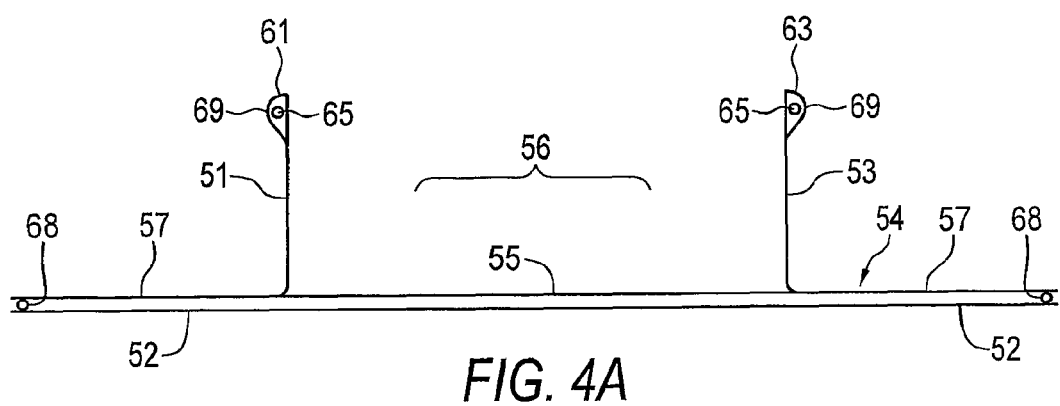
FIG. 4A is a cross-section taken along line 4-4 of FIG. 3 (not to scale)
Figure 4B:
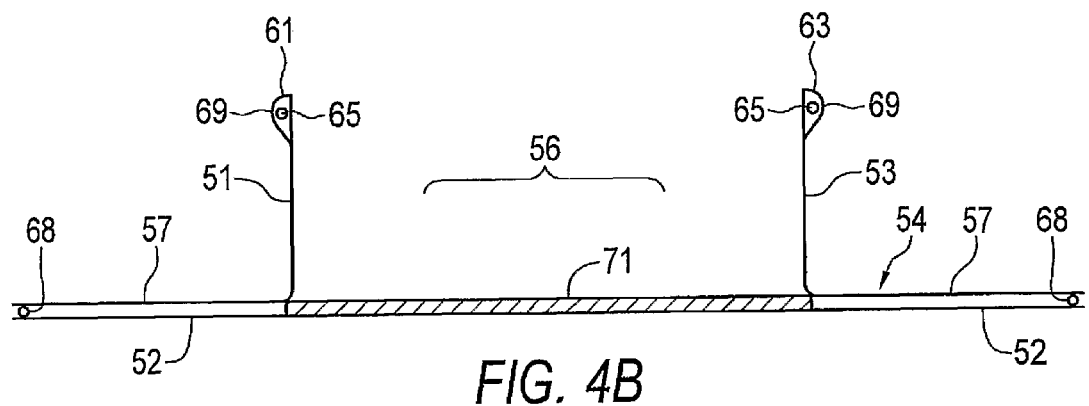
FIG. 4B is a cross-section taken along line 4-4 of FIG. 3 (not to scale) showing a first method of attaching a stabilizing layer.

In order to stabilize the shell during the manufacturing and packaging process after the shell is cut to length, and to facilitate the positioning of insert 70 within the shell 50 when the mother is replacing it, preferably the shell 50 is manufactured using a more rigid, less pliant material in crotch area 56 by providing a stabilizing material in that area to give greater rigidity to the diaper. For example, the waterproof non-absorbent layer 55 may be replaced with a layer of less pliant material 71 glued to sheet 52 as shown in FIG. 4B. Preferably layer 71 is a layer of flexible, resilient waterproof plastic material such as a closed cell, expanded low-density polyethylene referred to as PE foam from 1 to 5 mm in thickness, preferably about 2 mm thick. A suitable material for example is the PE foam underlayment sold by Goodfellow as 2.0 floating foam. Such material can be ecologically friendly in that it is blown with butane. Further the plastic which is used may be degradable, bio-degradable and/or compostable. The material for and thickness of the stabilizer layer 71 is selected so that it is soft and resilient in order to be comfortable for the baby, yet retains its shape when released. The material for and thickness of the stabilizer is selected so that it provides the desired cupping of the shell 52 and opening and separation of the leg gathers 61, 63 to facilitate placement and removal of the insert 70 as described below.

Preferably the foam stabilizer layer 71 is hourglass-shaped and extends the full length of the crotch area 56, however shorter lengths or rectangular or other shapes will also be effective. The foam stabilizer layer 71 may have holes cut in it in an appropriate size and pattern in order to permit heat to escape which builds up between the diaper shell and the absorbent insert. For example, it may be provided with an array of small apertures or a few larger apertures. For increased stiffness it may be formed as a textured layer having, for example, a stamped pattern providing a pattern of shallow raised edges or thickenings for strength, such as a cross-hatching, checkerboard or pattern of hollow circles, squares, rectangles, bubbles or other patterns for purposes of rigidity.

Figure 4C:
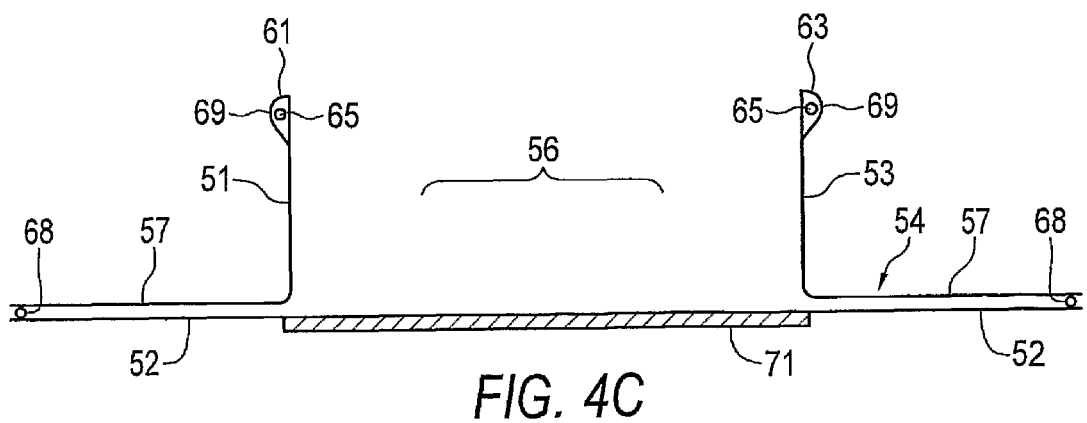
FIG. 4C is a cross-section taken along line 4-4 of FIG. 3 (not to scale) showing a second method of attaching a stabilizing layer.
Figure 4D:
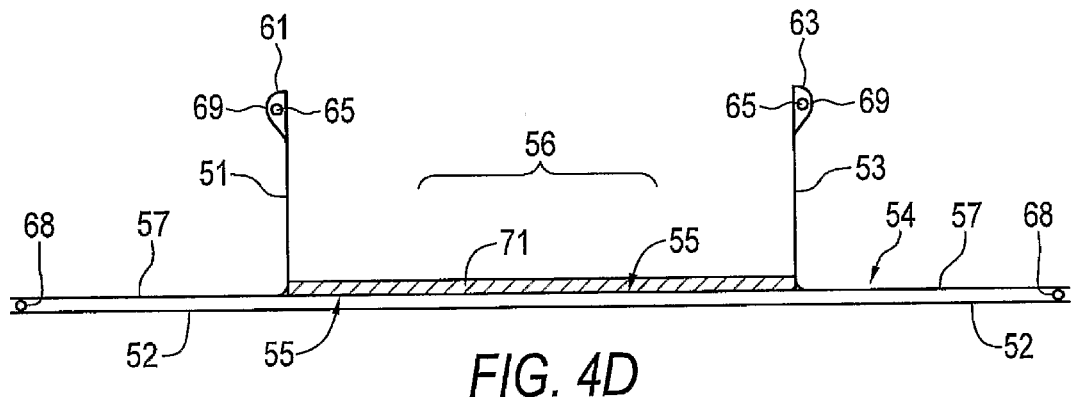
FIG. 4D is a cross-section taken along line 4-4 of FIG. 3 (not to scale) showing a third method of attaching a stabilizing layer.
Figure 4E:
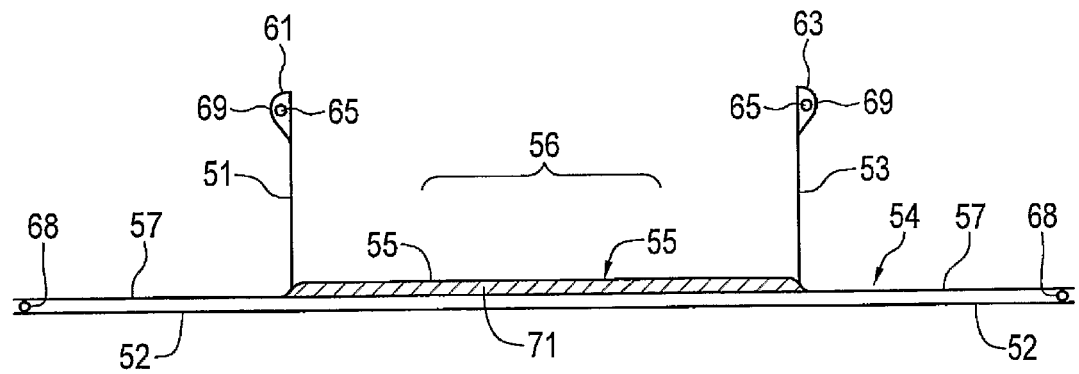
FIG. 4E is a cross-section taken along line 4-4 of FIG. 3 (not to scale) showing a fourthmethod of attaching a stabilizing layer.

FIG. 4B is a cross-section taken along line 4-4 of FIG. 3 (not to scale) showing the first method of attaching a stabilizing layer 71 by being glued to the upper surface of back sheet 52 in the crotch area 56. The foam stabilizer 71 may be fixed in the diaper shell in various other ways besides being glued to the upper surface of back sheet 52 in the crotch area 56. FIG. 4C is a cross-section taken along line 4-4 of FIG. 3 (not to scale) showing a second method of attaching a stabilizing layer 71 by gluing to the outside surface of back sheet 52 in the crotch area 56. FIG. 4D and 4E are cross-sections taken along line 4-4 of FIG. 3 (not to scale) showing third and fourth methods of attaching a stabilizing layer 71 where a separate inner central sheet 55 is attached to the inner leg gathers 61, 63. The foam stabilizer layer 71 can be glued to the upper or lower surfaces of inner central sheet 55 as in FIG. 4D and 4E. In all cases it is preferred that the diaper shell can be manufactured on a current state of the art disposable diaper machine.

Other methods of stiffening and stabilizing the crotch area 56 of shell 50 in the same way as the foam stabilizer layer 71 may be used. A web or net of plastic ridges or ribs may be formed on the inner surface of sheet 52 in the crotch area 56. The additional rigidity in crotch area 56 may also be provided by sandwiching a thin layer of air-laid absorbent or pulp in the manufacturing process between sheets 52 and 55 provided that sheet 55 is liquid impermeable so that the stiffening absorbent layer is not exposed to liquid in the crotch area. For example in the existing disposable diaper structure the amount of pulp 16 in the crotch area could be reduced, super absorbent polymers omitted and cover sheet 15 replaced with a waterproof sheet. Gluing of the pulp pad 16 to the cover sheet 15 would then add extra stability. Again, in order for the diaper to be comfortable and wearable by an infant, the stiffening layer must still have the flexibility in the crotch area comparable to that of current disposable diapers. Similarly an existing disposable diaper structure 10 could be used in the present invention by providing a waterproof membrane over the absorbent pad 16, either secured to the diaper by fixed or releasable adhesive or as a separate liner. The diaper would then serve as the re-usable shell 50 and the pad 16 would function as the stabilizing layer 71.

To make diaper shell 50 re-usable, a disposable absorbent insert 70 (FIG. 5) is provided to be removably inserted in crotch area 56. Insert 70 is sized to fit snugly up against leg gathers 61, 63 (or cuffs 62, 64 in FIG. 9) along either edge 72, 74 and not to extend beyond the waist areas. Insert 70 has an absorbent pad 75 which may be manufactured from any of the existing absorbent materials such as fluff, super-absorbent polymer, or fibrous super-absorbent polymer but is preferably an ultra-thin air-laid pulp and polyolefin web with thermally-bonded super-absorbent polymers of the type manufactured by Thermacore™. Such air-laid pads provide greater absorbency with less material and less bulk and thickness. The absorbent pad 75 is preferably wrapped in a layer 76 of non-woven hydrophilic material to keep the skin of the infant from the pad. The pad has protective covers 80 which are formed of hydrophobic material and have elastic members 82 bonded thereto. Preferably the protective covers 80 wrap loosely around pad 75 and are secured along a single glue or heat welding line at 84. Covers 80 may also be attached to pad 75 along edges 72, 74. The covers may be provided with a releasable adhesive along the lower surface of edges 86 to attach to the interior surface 57 of shell 50.

Figure 6:
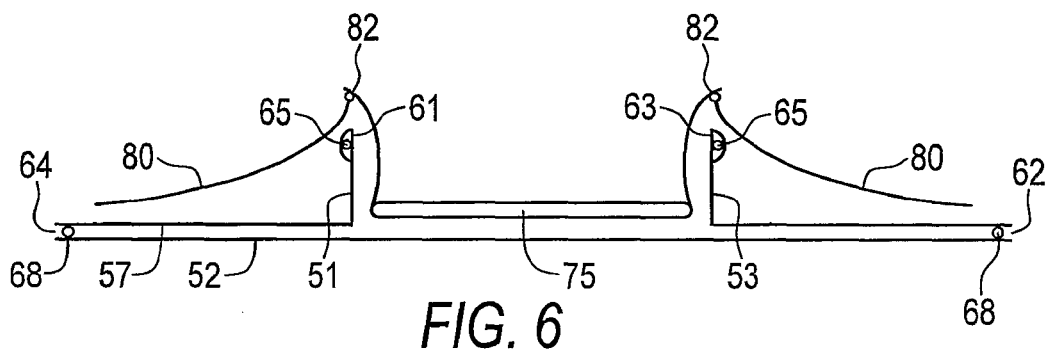
FIG. 6 is a cross-section illustrating the replaceable absorbent pad in a first configuration in the re-usable shell of FIG. 3 (not to scale) taken along lines 4-4.
Figure 7:
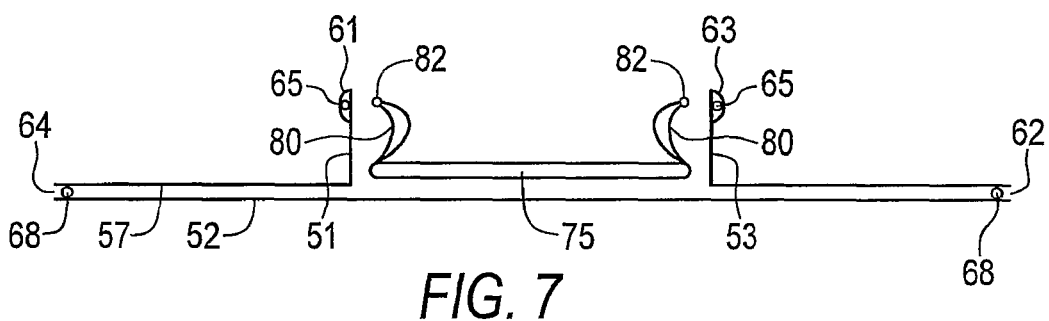
FIG. 7 is a cross-section illustrating the replaceable absorbent pad in a second configuration in the re-usable shell of FIG. 3 (not to scale) taken along lines 4-4.
Figure 8:
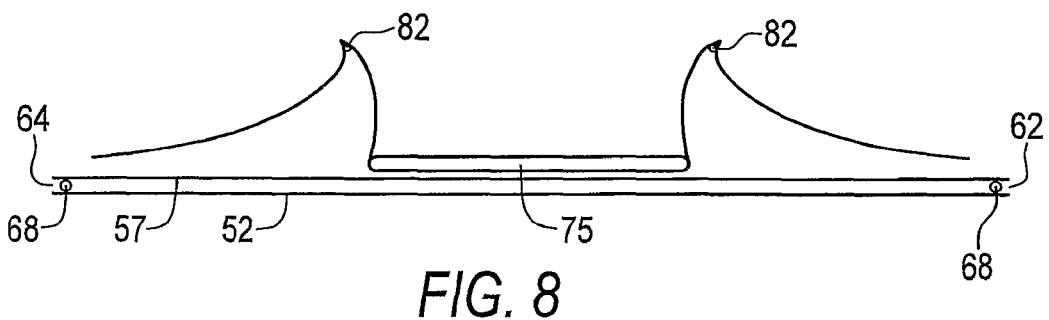
FIG. 8 is a cross-section (not to scale) illustrating the replaceable absorbent pad in the re-useable shell of FIG. 9, taken along lines 8-8.

As shown in FIG. 6, by extending the wings over leg gathers 61, 63, the waterproof protective covers 80 protect the shell from being soiled and improve its re-usability. Elastic members 82 serve to elevate the covers 80 above the leg gathers 61, 63. Further, when removing and replacing insert 70, covers 80 are used by the mother as handles to remove the insert and then as a wrap to remove and dispose of the contents. Alternatively the mother can place the soiled insert 70 into a bio-degradable plastic disposal bag. Where the shell has no leg gathers, as in the shell 90 in FIG. 9, the protective covers 80 form the leg gathers as in FIG. 8. Where the protective covers 80 are not extended over the leg gathers 61, 63 they can form a second leg gather as shown in FIG. 7 to assist in retaining the waste material in the crotch area 56. Where leg gathers 61, 63 are provided, the pad 75 fits snugly up against leg gathers 61, 63 along either edge 72, 74 and does not extend beyond the waist areas, as described above, and thereby fits within the channel formed by the leg gathers 61, 63. To assist the mother in properly locating the insert, particularly as in the embodiment shown in FIG. 9, the interior of shell 50 may be provided with markings or lines 92 for alignment (FIG. 9) with corresponding markings 94 on insert 70. The lower surface 85 of insert 70 may also be provided with strips of releasable adhesive, protected by removable paper cover strips until in use, in order to assist the mother in securing the insert 70 in place.

Where the covers 80 form a second interior leg gather it can be the same height as leg gathers 61, 63, or will also function if it is higher or lower. Where the re-usable shell 50 has double leg gathers and the covers 80 form a third pair of interior leg gathers, the height of all the leg gathers can be the same. Or alternatively each of the pairs of leg gathers can have different heights or two of the three pairs of leg gathers have the same height, with the third pair having a different height. The tension of the elastic on each pair of leg gathers can similarly be the same as between the re-usable shell and the replaceable insert or one or the other can have a tighter tension.

The insert 70 is manufactured as a separate element and may be packaged and sold separately to the consumer. When sold separately as such, the covers 80 may be folded on top or bottom of pad 75 or completely around the pad. A mother may then choose to insert the insert 70 in a standard disposable diaper to act as a diaper doubler either without unfolding covers 80, or by extending the covers 80 to protect the diaper for subsequent re-use. Preferably the shell 50 is packaged with an insert 70 already inserted. In that case an insert 70 can be inserted in shell 50 during the manufacturing process as described below, or after the manufacturing of same and prior to packaging. Shell 50 can similarly be packaged for the consumer without an insert 70 inserted therein but rather provided separately. The protective covers 80 can be pre-pressed or folded or packaged in a way that facilitates the covers sitting over interior leg gathers 61, 63 in the most effective position to keep the interior of the shell as clean as possible, such as by folding them under the pad during packaging, or providing double folds.

To use the invention where an insert 70 is inserted prior to packaging, the consumer will apply the diaper to the infant in the usual way as with the conventional disposable diaper. After the pad 75 has been wet or soiled, the insert 70 is removed from shell 50 by grasping covers 80, covers 80 are wrapped around the waste-containing pad 75, secured by the releasable adhesive or placed in a degradable disposal bag, and placed in a waste disposal container or compost. Shell 50 can then be rinsed, and a replacement insert 70 is inserted.

After one or more replacement inserts 70 have been similarly used, the shell 50 can be discarded and a new shell 50 and insert 70 used. In this way, the re-usable diaper shell 50 may be re-used once or several times until it also becomes soiled or the adhesive straps 58 are inoperative. The re-usable diaper shell 50 can be manufactured from more durable materials so that it is can be machine washed and can be manufactured from a durable cloth material, either sewn or glued using existing disposable diaper manufacturing processes. In this way the diaper shell can be reused at least once and perhaps several times, thereby reducing the consumption of materials and the resulting expense and waste. At the same time, no significant amount of additional work or energy is required by the mother in terms of washing.

Figure 10:
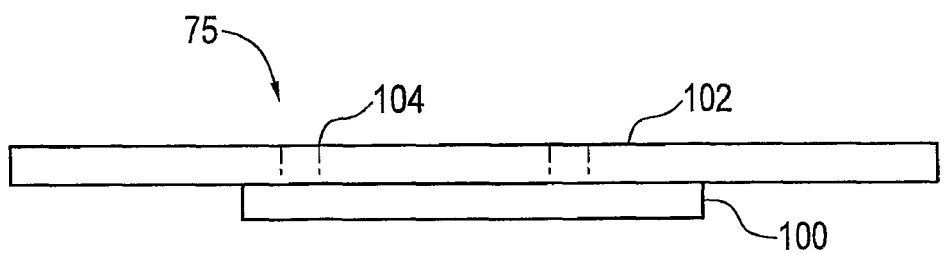
FIG. 10 is a front elevation of a second embodiment of the replaceable absorbent pad.

Pad 75 can also have two or more layers, including a narrower central layer 100, to provide more absorbency in the central crotch area while minimizing the amount of absorbent material, as illustrated in FIG. 10 with protective covers 80 removed for ease of illustration. The upper layer 102 can have perforations 104 of various shapes and arrays to ensure that large flows of liquid are slowed down, exposed to a greater absorbent surface area and held in the central area long enough to be absorbed. Differing widths and thicknesses of layer 100 and differing amounts and types of super absorbent polymers provide different levels of absorbency and cost.

Figure 11:
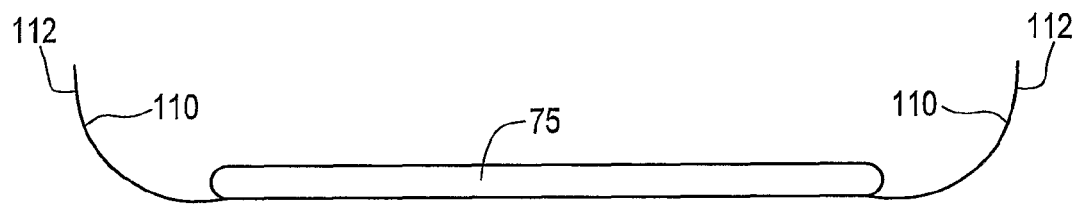
FIG. 11 is a cross-section (not to scale) illustrating a further embodiment of the replaceable absorbent pad.
Figure 12:
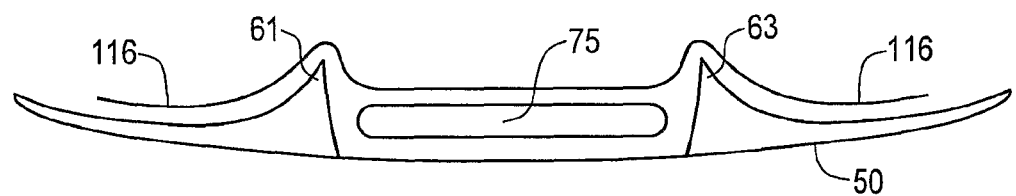
FIG. 12 is a cross-section (not to scale) illustrating a further embodiment of the replaceable absorbent pad in a further configuration in the re-usable shell.
Figure 13:
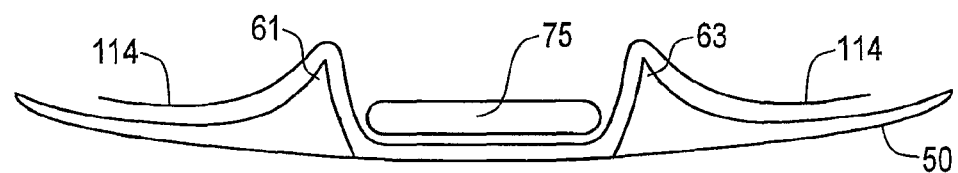
FIG. 13 is a cross-section (not to scale) illustrating a further embodiment of the replaceable absorbent pad in a further configuration in the re-usable shell.

While the foregoing embodiment of disposable insert 70 is preferred, the two-piece diaper system of the invention will also function with different embodiments of the removable insert 70. For example, insert 70 may be produced without elastic members 82. In that case the covers 80 are pre-folded to provide the shape shown in FIG. 5 and may have a releasable adhesive along the lower surfaces of edges 86 to attach to the shell 50. Alternatively a pad 75, without covers 80, can be used as the removable insert, in which case the re-usable shell 50 is kept less clean between changes. As an intermediate embodiment the covers 80 may be short side extensions 110 as shown in FIG. 11, to form a U-shaped channel which does not extend over leg gathers 61, 63. Releasable adhesive may be applied at 112 to retain extensions 110 in place against the leg gathers 61, 63. As a further embodiment shown in FIG. 13, a non-porous cover sheet 114 could be used below pad 75 without covers 80, with the sheet 114 either unattached, or attached to pad 75 by releasable adhesive. In that way the mother could re-use the non-porous cover sheet. As a further embodiment shown in FIG. 12, pad 75 without covers 80 can be used with a porous cover sheet 116 over the pad as in FIG. 13 so that the stool is contained by cover sheet 116 and the shell kept cleaner. As a further alternative, a mother could use a separate pad 75, without covers 80, to place on top of insert 70 (FIG. 5) in the shell 50. This would provide more absorbency at nighttime and more flexibility during the day as only the extra pad 75 would require replacement in some instances.

Existing machines for manufacturing disposable diapers, such as those manufactured by Fammeccanica, PCMC, Joa and Cellulose Converting Equipments, utilize a continuous line in which a ribbon of the absorbent pulp is formed and shaped, and fed on a supporting surface such as tissue, the outer poly sheet is unwound from below the pulp line and adhesive and leg elastic are applied to it. The absorbent layer is then applied to the poly sheet, and a non-woven topsheet is applied over the pulp layer and bonded to the poly back sheet, the elasticized leg gathers and tape tabs are applied and the diapers are then cut and folded. In the preferred method of manufacturing the present invention, the shell 50 is manufactured in the same manner as conventional diapers but without including any sandwiched absorbent layer, while absorbent insert 70 is manufactured separately. The inserts 70 are manufactured from air laid, thermal bonded air laid Super Absorbent Polymers technology roll stock. The non-woven pad cover and waterproof protective covers 80 with elastic members 82 are attached to the pad, and the inserts are cut to length, folded and packaged. The initial inserts 70 can be inserted into shells 50 during the manufacturing process by providing the finished but uncut inserts 70 on a continuous roll which is fed into the line of shells on the diaper line prior to cutting of the individual diapers.

While preferably the re-usable diaper shell 50 has no exposed absorbent material to ensure that it can be rinsed or washed and re-used, the present invention provides a system with variable components to allow the consumer to select a particular level of performance and cost of the product. Insert 70 may have a high absorbency pad 75 for night-time use and a thinner lower absorbency pad 75 for daytime use. Insert 70 can be provided with a stay-wet pad 75 for toilet training purposes. Shell 50 can be manufactured using biodegradable plastics or washable synthetics or cloth for a premium product and non-biodegradable material for an economical product. The insert 70 may have other selected features such as scent, disinfectant or anti-bacterial additives or bio-degradability to be used in combination with different shells. By selecting the appropriate absorbent materials and plastics, the insert 70 can be made to be completely compostable. Further, as described above, multiple layer pads 75 with differing widths and thicknesses of layer 100 will provide different levels of absorbency and cost. Thus the consumer can select variable degrees of performance, re-usability and bio-degradability of the combined shell 50 and insert 70, which will also affect the price of the product.

In a preferred form of the present invention the outer shell 50 is formed of a biodegradable plastic material such as products manufactured by Plastics Solutions Inc. of Vancouver, British Columbia. Also, for example, outer sheet 52, inner sheets 55, 57, non-wovens 76 and covers 80 can be made from a compostable polyester plastic such as the compostable plastic films manufactured by Plastic Solutions Inc., Heritage Plastics Inc. and Marshall Plastics, or other suitable plastic to make the insert 70 fully compostable and shell 50 at least partly degradable. While such materials are more expensive than non-biodegradable plastics, the re-usability of the shell 50 makes it economical. The fact that the shell is re-used several times makes the cost of the diapers in the present system, even using more expensive film, competitive with standard, single use disposable diapers. Materials which are desirable for use in the shell or elsewhere in the diaper due to superior physical characteristics such as biodegradability, or breathability, but which have been commercially unacceptable to date due to cost, will be more acceptable for use in the present invention due to the multiple uses possible for each re-usable shell and the resultant reduction in cost per use. The compostable plastic film is also found to have excellent printing qualities, so the diaper brand can be advertised on the exterior of the diaper shell and/or third party products or trademarks displayed and promoted.

Composting of disposable diapers has not to date been a viable option. However, the two-part diapering system of the present invention will facilitate composting of part or all of the disposable diaper. Since the soiled pad 75 with biosolids can be separated from the shell 50, the shell 50 can be composted if manufactured of compostable materials. As noted above, there are several different types of plastic films that will compost, such as polyethylene plus an additive that accelerates degradation. Such products must comply with ASTM D6400 "Standard Specification for Compostable Plastics" or ASTM D6868 and/or have BPI certification (Biodegradable Products Institute). The ASTM standard states that a product will compost in a certain minimum way. Without the approval governments, Federal, State and Municipal and most composters will not buy or use the product. By using a compostable plastic film and non woven in the disposable insert 70, that possess the appropriate physical characteristics for the use in diapers and also have the appropriate ASTM and/or BPI approvals required for composting, the cost of the diaper is still economic given the competing costs, and the insert 70 can be compostable. In addition, the petroleum based super absorbent polymers in pad 75 are replaced with a starch-based super absorbent polymer. Currently this is not done in single use diapers because the performance of the starch-based super absorbent polymer is inferior to petroleum based and therefore more super absorbent polymer has to be added and the starch-based super absorbent polymer is already more expensive then the petroleum-based product. Therefore the conventional wisdom in the diaper industry is that starch based super absorbent polymer is not currently a product that will work in the diaper industry. The two piece system of the present invention does not have this problem and can absorb the differences in cost between the two super absorbent polymer products, making either a compostable absorbent insert, a compostable re-usable shell or an entirely compostable product possible.

It is possible with the present invention to obtain the same results from one shell and three inserts as is obtained from three current disposable diapers. The shell 50, being non-absorbent and waterproof can be rinsed with a soap cleaning solution and a few drops of disinfectant if desired, or washed by hand or machine for re-use after each diaper change. The present invention therefore assists in the goal of reducing a consumer's carbon footprint by reducing, re-using and recycling the plastic and hydrocarbon-based material. This is accomplished by a) reducing the consumption of materials and energy through thinner, more efficient absorption pads and multiple uses of the diaper shell, thereby reducing shipping costs, landfill and energy required for manufacturing, laundering and/or disposal and hauling away; b) the diaper shell is re-used, possibly multiple times, thereby providing an efficient way to reduce the use of plastic; and c) the economies of the system permit more expensive, biodegradable materials to be used and still permit the product to compete with non-biodegradable materials. Further the diaper system can be manufactured using existing conventional disposable diaper machines, eliminating the need for expensive new equipment. The carbon credits earned by the consumer on purchasing the present diaper system can be translated into a discount to the consumer retail price in exchange for the manufacturer retaining the credits to permit the manufacturer to deal with or trade in a large volume of carbon credits.

As will be apparent to those skilled in the art in the light of the foregoing disclosure, many alterations and modifications are possible in the practice of this invention without departing from the spirit or scope thereof. While the invention has been described in the context of an infant diaper it is also applicable to adult incontinence diapers and children's pull-ups. Thus while a number of exemplary aspects and embodiments have been discussed above, those of skill in the art will recognize certain modifications, permutations, additions and sub-combinations thereof.

What is claimed is:

1. A diapering system comprising:
    a) a disposable re-usable diaper shell comprising:
        i) a pliant non-absorbent, liquid impervious body for removable fitting to the wearer, forming an interior and an exterior surface, a front and back portion, opposed side edges and a crotch area when so fitted;
        ii) opposed, non-absorbent liner portions secured along the opposed side edges of the body and forming opposed elastically contractible leg cuffs extending along either opposed side edges between the front and back portion, and opposed elastically contractible interior leg gathers spaced inwardly from said leg cuffs and extending between the front and back portion, the opposed elastically contractible leg gathers thereby defining a central channel region of said diaper shell between the opposed leg gathers extending between the front and back portion, the central channel region being without absorbent material which is exposed to contact with liquid in the crotch area and wherein the central channel region is stiffened by providing in the central channel region flexible material which is less pliant than said pliant non-absorbent, liquid impervious body to thereby stabilize said diaper shell for insertion of an absorbent insert; and
    b) a removable, replaceable absorbent insert comprising an absorbent pad comprising a body of absorbent material having a non-woven hydrophilic covering, said insert being sized and shaped to be retained adjacent the interior surface of the diaper shell in the central channel region.

2. The diapering system of claim 1 wherein said removable, replaceable absorbent insert comprises attached hydrophobic covers extending from opposed sides of said absorbent pad and extending over said interior leg gathers and a portion of the interior surface of said pliant non-absorbent, liquid impervious body when in operative position.

3. The diapering system of claim 2 wherein the hydrophobic covers have elongated elastic members secured thereto to form leg gathers when in operative position.

4. The diapering system of claim 1 wherein said flexible material which is less pliant than said pliant non-absorbent, liquid impervious body comprises a layer of non-absorbent plastic material secured to the non-absorbent, liquid impervious interior surface in said central channel region.

5. The diapering system of claim 4 wherein said layer of non-absorbent plastic material comprises a polyethylene foam.

6. The diapering system of claim 1 wherein said pliant, non-absorbent, liquid impervious body comprises a plastic film.

7. The diapering system of claim 6 wherein said plastic film comprises a biodegradable film.

8. The diapering system of claim 1 wherein said flexible material which is less pliant than said pliant non-absorbent, liquid impervious body comprises a layer of absorbent material covered by a waterproof layer whereby said absorbent material is not exposed to contact with liquid in the central channel region.

9. The diapering system of claim 1 wherein said flexible material which is less pliant than said pliant non-absorbent, liquid impervious body comprises a layer of non-absorbent plastic material secured to the non-absorbent, liquid impervious outer surface in said central channel region.

10. A disposable re-usable diaper shell comprising a pliant non-absorbent, liquid impervious body for removable fitting to the wearer, forming an interior and an exterior surface, a front and back portion, opposed side edges and a crotch area when so fitted, said diaper shell comprising opposed, non-absorbent liner portions secured along said opposed side edges of said body and forming opposed elastically contractible leg cuffs extending along either opposed side edges between said front and back portion, and opposed elastically contractible interior leg gathers spaced inwardly from said leg cuffs and extending between the front and back portion, said opposed elastically contractible leg gathers thereby defining a central channel region of said diaper shell between said opposed leg gathers extending between said front and back portion, the central channel region being without absorbent material which is exposed to contact with liquid in the crotch area and wherein the central channel region is stiffened by providing in the central channel region flexible material which is less pliant than said pliant non-absorbent, liquid impervious body to thereby stabilize said diaper shell for insertion of an absorbent insert, said central channel region being adapted for removably receiving an absorbent pad in said central channel region.

11. The disposable re-usable diaper shell of claim 10 wherein said flexible material which is less pliant than said pliant non-absorbent, liquid impervious body comprises a layer of non-absorbent plastic material secured to the non-absorbent, liquid impervious interior surface in said central channel region.

12. The diaper shell of claim 11 wherein said layer of non-absorbent plastic material comprises a polyethylene foam.

13. The disposable re-usable diaper shell of claim 10 wherein said pliant, non-absorbent, liquid impervious body comprises a plastic film.

14. The diaper shell of claim 13 wherein said plastic film is compostable.

15. The diaper shell of claim 13 wherein said plastic film comprises a biodegradable film.

16. The disposable re-usable diaper shell of claim 10 wherein said flexible material which is less pliant than said pliant non-absorbent, liquid impervious body comprises a layer of absorbent material covered by a waterproof layer whereby said absorbent material is not exposed to contact with liquid in the central channel region.

17. The disposable re-usable diaper shell of claim 10 wherein said flexible material which is less pliant than said pliant non-absorbent, liquid impervious body comprises a layer of non-absorbent plastic material secured to the non-absorbent, liquid impervious outer surface in said central channel region.

18. In combination in a package, the diaper shell of claim 10 and a plurality of absorbent pads adapted to be removably placed in said central channel region of said diaper shell.

19. A method of manufacturing a diaper shell without absorbent material which is exposed to contact with liquid in the crotch area thereof and adapted for removably inserting an absorbent pad, said method comprising bonding in a continuous process a sheet of non-woven hydrophobic liner material to a sheet of liquid impervious backsheet material, and cutting said bonded sheets to form a disposable diaper shell comprising a non-absorbent, liquid impervious body and a non-absorbent liner having opposed elastically contractible leg cuffs and opposed elastically contractible interior leg gathers spaced inwardly from said leg cuffs, the opposed elastically contractible leg gathers thereby defining a central channel region of said diaper shell between the opposed leg gathers, said diaper shell being without absorbent material in said central channel region which is exposed to contact with liquid in the central channel region and wherein the central channel region is stiffened by providing in the central channel region flexible material which is less pliant than said pliant non-absorbent, liquid impervious body to thereby stabilize said diaper shell for insertion of an absorbent insert in said central channel region.

20. The method of claim 19 wherein said flexible material which is less pliant than said pliant non-absorbent, liquid impervious body comprises a layer of non-absorbent plastic material secured to the non-absorbent, liquid impervious interior surface in said central channel region of said body.

21. The method of claim 19 wherein said flexible material which is less pliant than said pliant non-absorbent, liquid impervious body comprises a layer of absorbent material covered by a waterproof layer whereby said absorbent material is not exposed to contact with liquid in the central channel region.

22. The method of claim 19 wherein said flexible material which is less pliant than said pliant non-absorbent, liquid impervious body comprises a layer of non-absorbent plastic material secured to the non-absorbent, liquid impervious outer surface in said central channel region.

* * * * *